United States Patent
Lescouzeres et al.

[11] Patent Number: 5,907,765
[45] Date of Patent: May 25, 1999

[54] METHOD FOR FORMING A SEMICONDUCTOR SENSOR DEVICE

[75] Inventors: Lionel Lescouzeres; Jean Paul Guillemet; Andre Peyre Lavigne, all of Toulouse, France

[73] Assignee: Motorola, Inc., Schaumburg, Ill.

[21] Appl. No.: 08/669,013

[22] Filed: Jun. 24, 1996

[30]      Foreign Application Priority Data

Jun. 30, 1995  [FR]  France .................................. 95 07903

[51] Int. Cl.⁶ ................................................ H01L 21/62
[52] U.S. Cl. .................. 438/49; 438/52; 438/53
[58] Field of Search .................................. 438/49, 52, 53, 438/702, 703, FOR 412, FOR 432, FOR 438; 257/414, 522

[56]               References Cited

U.S. PATENT DOCUMENTS

| 4,740,387 | 4/1988 | Manaka . |
| 4,849,050 | 7/1989 | Evans et al. . |
| 4,849,071 | 7/1989 | Evans et al. . |
| 4,967,589 | 11/1990 | Yagawara et al. . |
| 5,095,401 | 3/1992 | Zavracky et al. . |
| 5,164,339 | 11/1992 | Gimpelson . |
| 5,316,619 | 5/1994 | Mastrangelo . |
| 5,345,213 | 9/1994 | Semancik et al. . |
| 5,373,181 | 12/1994 | Scheiter et al. . |
| 5,489,556 | 2/1996 | Li et al. . |

FOREIGN PATENT DOCUMENTS 0313390   4/1989   European Pat. Off. .

Primary Examiner—George R. Fourson
Attorney, Agent, or Firm—Harry A. Woliln; Rennie William Dover; Daniel R. Collopy

[57]                ABSTRACT

A method for forming a semiconductor sensor device comprises providing a substrate (4) and forming a sacrificial layer (18) over the substrate. The sacrificial layer (18) is then patterned and etched to leave a portion (19) on the substrate (4). A first isolation layer (6) is formed over the substrate (4) and portion (19) of the sacrificial layer and a conductive layer (12), which provides a heater for the sensor device, is formed over the first isolation layer (6). The portion (19) of the sacrificial layer is then selectively etched to form a cavity (10) between the first isolation layer (6) and the substrate (4), the cavity (10) providing thermal isolation between the heater and the substrate.

13 Claims, 6 Drawing Sheets

METHOD FOR FORMING A SEMICONDUCTOR SENSOR DEVICE

FIELD OF THE INVENTION

This invention relates to semiconductor sensor devices and a method for forming semiconductor sensor devices. More particularly, this invention relates to semiconductor chemical sensors and a method for their manufacture.

BACKGROUND OF THE INVENTION

A chemical sensor is a device which monitors the concentration of a given chemical species in a liquid or a gas. Chemical sensors are used, for example, to detect unsafe levels of poisonous or explosive gases in the work and home environments.

Typically, chemical sensors comprise a sensitive layer, which is sensitive to a particular chemical which is to be detected by the sensor, and a heater. The heater increases the temperature of the sensitive layer to increase the sensitivity and selectivity of the sensor.

Chemical sensors formed using hybrid technology, such as for example sensors formed on ceramic substrates, are well known. It is also known to fabricate a semiconductor chemical sensor wherein the sensor and heater are integrated onto a silicon substrate.

These known chemical sensors, however, have poor thermal isolation between the heater and substrate which results in significant power consumption.

In order to reduce the power consumption in the semiconductor chemical sensors, it has been proposed to micromachine the backside of the bulk silicon to form a thin membrane under the heater. The thickness of the membrane is in the order of 2 microns. Although the thin membrane reduces power consumption, the thin membrane is fragile and liable to break during fabrication resulting in a loss in yield. Moreover, in view of the fragility of the membrane, the sensors have to be manually rather than automatically handled, which is extremely time consuming and so increases the cost of manufacture.

U.S. Pat. No. 5,345,213 describes a method for forming a semiconductor chemical sensor wherein the membrane is formed by surface micromachining and etching the silicon underneath the membrane using a mixture of ethylenediamine-pyrocatechol-water-pyrazine (EDP). However, EDP is an extremely dangerous chemical which is believed to be a carcinogen. It would be preferable to avoid using such a chemical.

It is therefore desirable to provide an improved semiconductor sensor device and an improved method for reducing power consumption in a semiconductor sensor device which does not suffer from the above prior art problems.

SUMMARY OF THE INVENTION

In accordance with a first aspect of the present invention there is provided a method for forming a semiconductor sensor device comprising the steps of:

providing a substrate;

forming a sacrificial layer over the substrate;

patterning and etching the sacrificial layer to leave a portion on the substrate;

forming a first isolation layer over the substrate and portion of sacrificial layer;

forming a conductive layer over the first isolation layer, the conductive layer providing a heater for the sensor device;

selectively etching the portion of sacrificial layer to form a cavity between the first isolation layer and the substrate, the cavity providing thermal isolation between the heater and the substrate;

forming a second isolation layer over the conductive layer; and forming a sensitive layer over the second isolation layer.

A semiconductor sensor device in accordance with the first aspect of the invention is also disclosed and claimed in claim 12 of the accompanying claims.

The patterning and etching step may comprise patterning and etching the sacrificial layer to leave first and second portions on the substrate, wherein the first and second portions of the sacrificial layer are selectively etched to provide first and second cavities between the first isolation layer and the substrate. Having more than one cavity is particularly advantageous in a semiconductor sensor device having a large surface area wherein additional support is required for the first isolation layer which forms the membrane of the sensor device.

In addition, a semiconductor sensor device having more than one cavity can have more than one sensor element on the same substrate, with each sensor element being thermally isolated from the other sensor elements. The temperature of the different sensor elements can be set at different values so that the sensor elements have different responses.

In accordance with a second aspect of the present invention there is provided a method for forming a semiconductor sensor device comprising the steps of:

providing a substrate;

forming a first isolation layer over the substrate;

etching the first isolation layer and substrate to form a trench;

filling the trench with sacrificial material;

forming a conductive layer over the first isolation layer and sacrificial material in the trench, the conductive layer providing a heater for the sensor device;

selectively etching the sacrificial material in the trench to form a cavity between the conductive layer and the substrate to provide thermal isolation between the heater and the substrate;

forming a second isolation layer over the conductive layer; and forming a sensitive layer over the second isolation layer.

A semiconductor sensor device in accordance with the second aspect of the invention is also disclosed and claimed in claim 13 of the accompanying claims.

The etching the first isolation layer and substrate step may comprise etching the first isolation layer and substrate to form first and second trenches and wherein the sacrificial material in the first and second trenches is selectively etched to form first and second cavities between the conductive layer and the substrate. As mentioned above, having more than one cavity is particularly advantageous in a semiconductor sensor device having a large surface area wherein additional support is required for the conductive layer which forms the membrane of the sensor device.

In accordance with a third aspect of the invention, the method further comprises the step of forming a third isolation layer underneath the conductive layer, the third isolation layer forming the membrane over the cavity.

It will be appreciated that the methods for forming a semiconductor device in accordance with the different aspects of the invention all provide semiconductor sensor devices having at least one cavity for providing thermal isolation between the substrate and the heater. By having at least one cavity, the semiconductor sensor devices in accordance with the invention have reduced heat loss and power consumption but do not have fragile membranes which make the devices difficult to handle. Furthermore, the present invention avoids the need to use dangerous chemicals, such as EDP, in the manufacturing process.

BRIEF DESCRIPTION OF THE DRAWINGS

Three semiconductor sensor devices in accordance with the invention and a method for forming the three semiconductor sensor devices in accordance with the invention will now be described, by way of example only, with reference to the accompanying drawings in which.

DETAILED DESCRIPTION OF THE DRAWINGS

Figure 1:
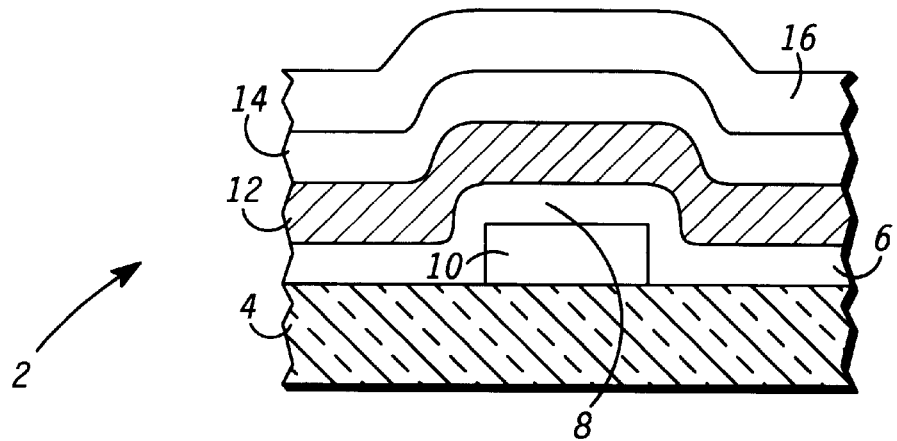
FIG. 1 shows a simplified schematic cross-sectional view of a semiconductor sensor device in accordance with a first embodiment of the present invention.

Referring firstly to FIG. 1, a semiconductor sensor device 2 in accordance with a first embodiment of the invention is shown comprising a substrate 4, a first isolation layer 6 formed over the substrate 4 to form a bridge 8, wherein a cavity 10 is formed between the first isolation layer 6 and substrate 4. A conductive layer 12, which layer forms the heater of the semiconductor sensor device 2, is formed over the first isolation layer 6. The electrodes for providing voltage to the heater are not shown. The cavity 10 provides thermal isolation between the first isolation layer 6 and the substrate 4. In the embodiment described herein, the cavity 10 is filled with air, however, the cavity may be filled with any material which provides good thermal insulation.

A second isolation layer 14 is formed over the conductive layer 12 and a sensitive layer 16 is formed over the second isolation layer 14.

The sensitive layer 16 is sensitive to the chemical species to be sensed by the sensor device. For example, in a carbon monoxide sensor, the sensitive layer 16 typically comprises a tin oxide layer.

Thus, by forming the isolation layer, which forms the sensor membrane, on a sacrificial layer and then subsequently etching the sacrificial layer so as to provide a cavity between the membrane and substrate, the present invention provides thermal isolation between the heater and the substrate but without the problems of the prior art devices mentioned above. The semiconductor sensor device in accordance with the invention provides reduced heat loss and reduced power consumption without providing a device which is fragile to handle. Moreover, no dangerous chemicals are required in such a devices manufacture.

A method for forming a semiconductor device in accordance with the first embodiment of the present invention will now be described with reference to FIGS. 1–7.

Figure 2:
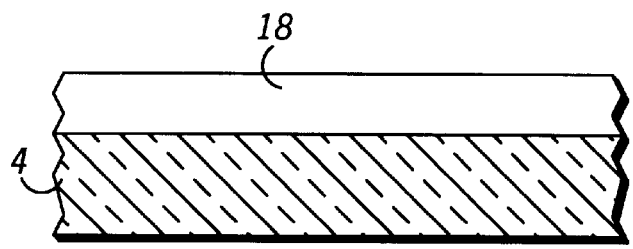
FIGS. 2–5 show simplified schematic cross-sectional views of the semiconductor sensor device of FIG. 1 during different stages of fabrication and according to the present invention.
Figure 3:
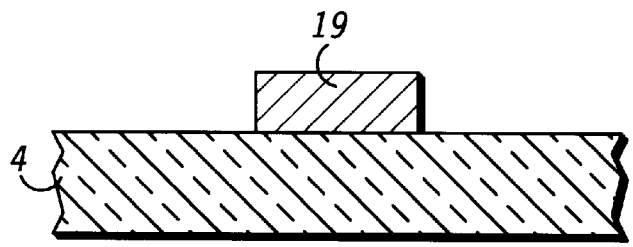
Figure 4:
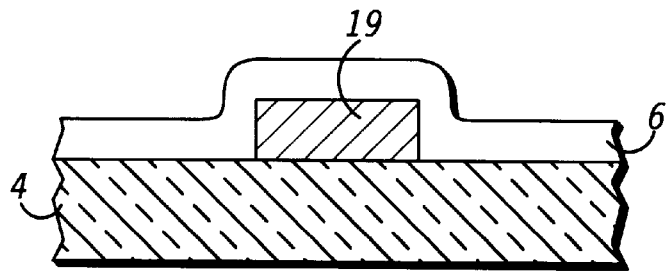
Figure 5:
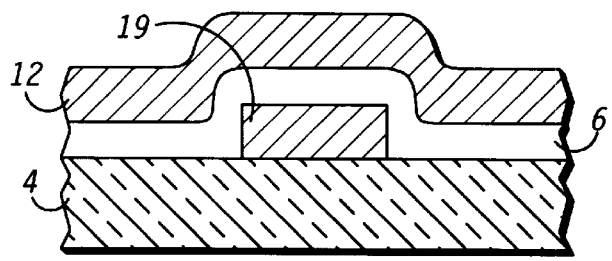
Figure 6:
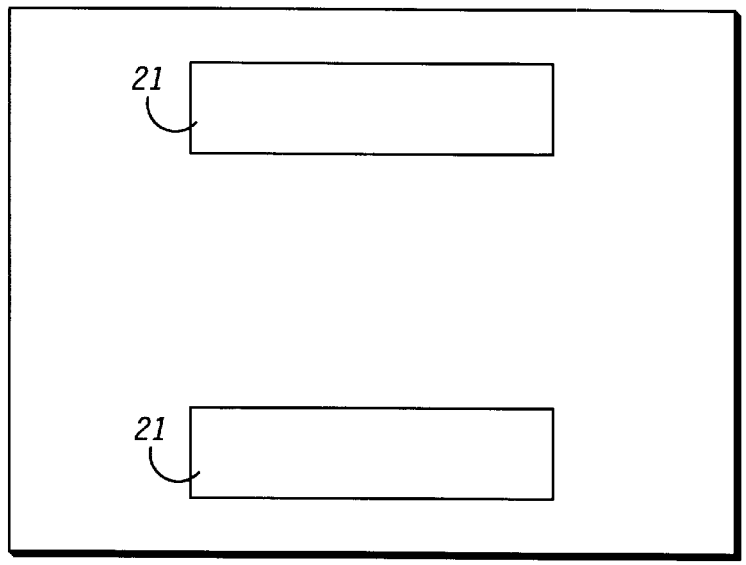
FIGS. 6 and 7 show simplified schematic plan views of the semiconductor sensor device of FIG. 1 during different stages of fabrication and according to the present invention.

Firstly, a substrate 4 is provided and a sacrificial layer 18 is formed over the substrate 4 (FIG. 2). The sacrificial layer is patterned and etched, as is well known in the art, to leave a portion 19 of the sacrificial layer on the substrate 4 (FIG. 3). A first isolation layer 6 is formed over the substrate and partially over the portion 19 of the sacrificial layer (FIG. 4). As can be seen from FIG. 6, the first isolation layer 6 is patterned and etched so as to leave part 21 of the portion 19 of the sacrificial layer exposed for subsequent etching.

Figure 7:
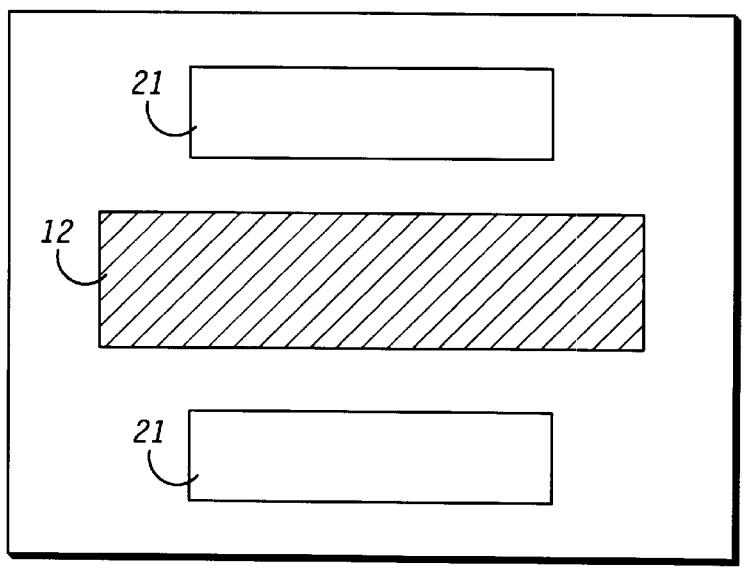

A conductive layer 12 is formed on the first isolation layer 6 (FIG. 5) but not on the exposed part 21 of the portion 19 of the sacrificial layer (see FIG. 7). The portion 19 of the sacrificial layer is then selectively etched using an isotropic etch (vertical and lateral etch), preferably using a liquid etchant. The type of etchant used depends on the materials of the sacrificial layer 18, isolation layer 6 and conductive layer 12. If, for example, the sacrificial layer comprises a silicon oxide layer, the isolation layer comprises a silicon nitride layer and the conductive layer comprises a polysilicon layer, liquid hydrogen fluoride can be used as the etchant to selectively etch the portion of the silicon oxide sacrificial layer.

After the portion 19 of the sacrificial layer has been selectively removed, a cavity 10 is provided between the first isolation layer 6 and the substrate 4: that is, the first isolation layer 6 forms a bridge 8.

A second isolation layer 14 is formed over the conductive layer 12 and a sensitive layer 16 is formed over the second isolation layer 14 (FIG. 1).

Figure 8:
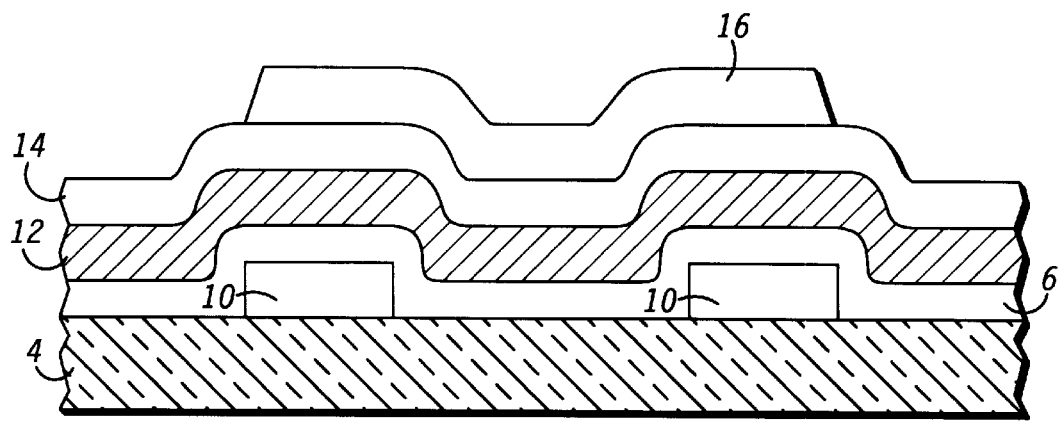
FIG. 8 shows a simplified schematic cross-sectional view of an alternative embodiment of the semiconductor sensor device shown in FIG. 1.

The semiconductor sensor device in accordance with the first embodiment of the invention has so far been described having one cavity 10. However, the sensor device in accordance with the invention may comprise two or more cavities, as shown for example in FIG. 8. This is particularly advantageous for sensors having a large surface area.

A further advantage of providing a semiconductor sensor device having two or more cavities is that it gives the option of having different sensor elements on the same chip which elements are thermally disconnected. In such a device, the temperatures of the different sensor elements can be set at different values to get different responses from the sensor elements.

In order to form such a sensor device, the above method is modified such that two portions 19 of the sacrificial layer are formed and then selectively etched.

In, for example, a carbon monoxide sensor device, the materials of the different layers may be as follows. A silicon oxide sacrificial layer is formed on a silicon substrate. The first isolation layer comprises silicon nitride. The conductive layer is formed from polysilicon material. The second isolation layer comprises silicon oxide. The sensitive layer comprises tin oxide. It is not, however, intended that the invention be limited to these types of layers or to carbon monoxide sensors. Those of skill in the art will understand based on the description given herein that various semiconductor and isolation materials can be used. For example, the isolation layers may be formed from oxynitride, oxide, or nitride, the sacrificial layer may be formed from oxide, doped oxide, or polyimide, the conductive layer may be formed from poly or metal, and the sensitive layer may comprise one of many different kinds of metal oxide.

Figure 9:
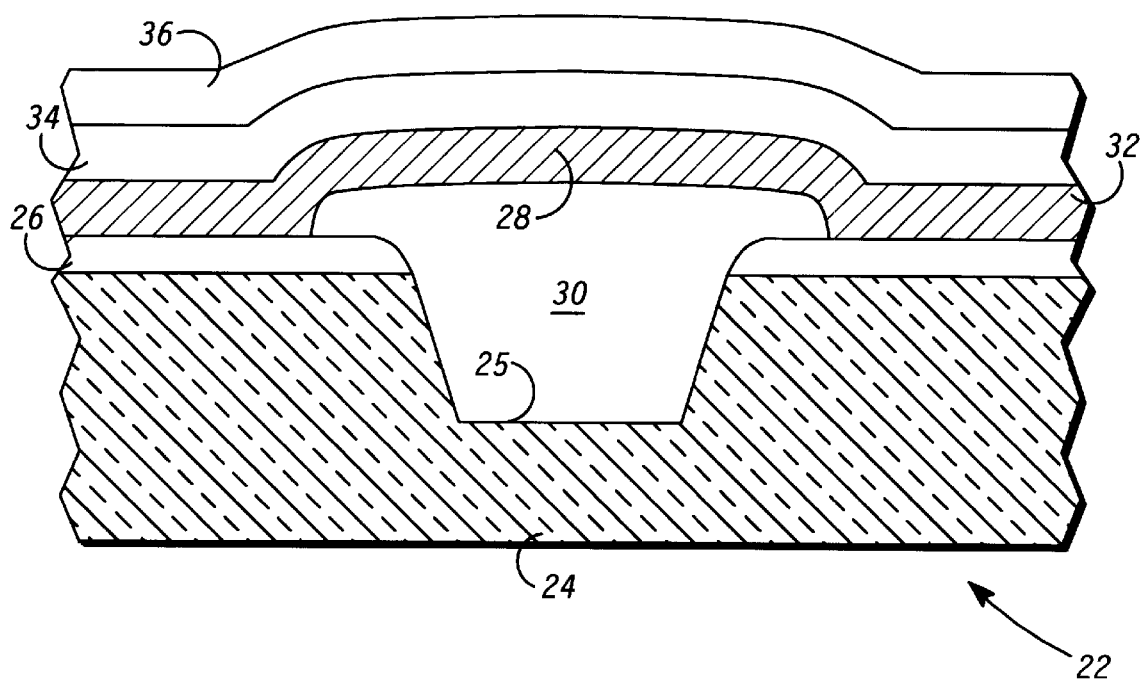
FIG. 9 shows a simplified schematic cross-sectional view of a semiconductor sensor device in accordance with a second embodiment of the present invention.

Referring now to FIG. 9, a semiconductor sensor device 22 in accordance with a second embodiment of the invention is shown comprising a substrate 24, a first isolation layer 26 formed over the substrate 24, a trench 25 extending downward through the first isolation layer 26 and into the substrate 24, and a conductive layer 32 formed over the first isolation layer 26 and trench 25 to provide a cavity 30 between the conductive layer 32 and bottom of the trench 25. The conductive layer 32 forms the heater of the semiconductor sensor device 22. The electrodes for providing voltage to the heater are not shown. The cavity 30 provides thermal isolation between the conductive layer 32 and the substrate 24. In the embodiment described herein, the cavity 10 is filled with air, however, the cavity may be filled with any material which provides good thermal insulation. A second isolation layer 34 is formed over the conductive layer 32 and a sensitive layer 36 is formed over the second isolation layer 34. The sensitive layer 36 is sensitive to the chemical species to be sensed by the sensor device. For example, in a carbon monoxide sensor, the sensitive layer 36 typically comprises a tin oxide layer.

A method for forming a semiconductor device in accordance with the second embodiment of the present invention will now be described with reference to FIGS. 9–13.

Figure 10:
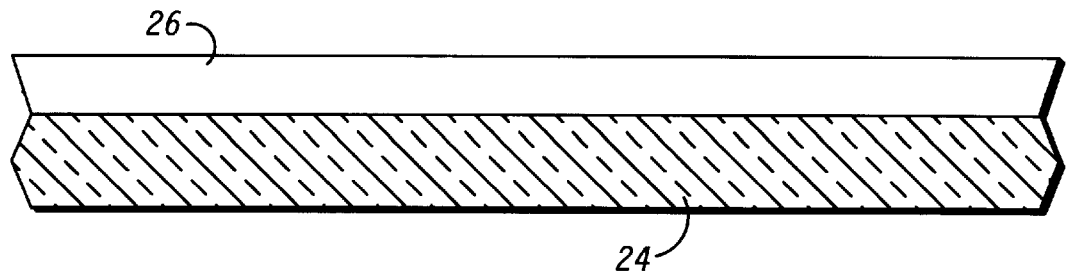
FIGS. 10–13 show simplified schematic cross-sectional views of the semiconductor sensor device of FIG. 9 during different stages of fabrication and according to the present invention.
Figure 11:
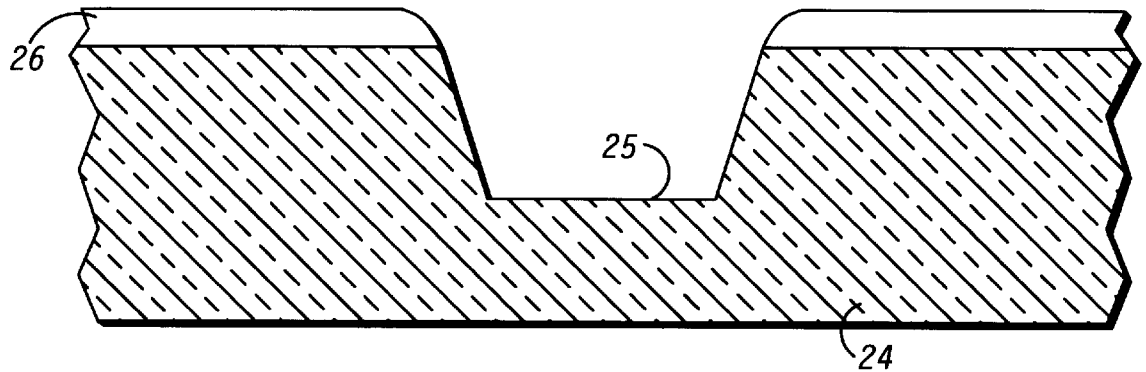

Firstly, a substrate 24 is provided and a first isolation layer 26 is formed over the substrate 24 (FIG. 10). The first isolation layer 26 is patterned and etched together with the substrate 24 to form a trench 25 through the first isolation layer 26 and into the substrate 24 (FIG. 11). For a silicon nitride isolation layer formed on a silicon substrate, a chemical etch using potassium hydroxide etchant can be used to form the trench 25. Other types of etching, such as plasma etching, may also be used.

Figure 12:
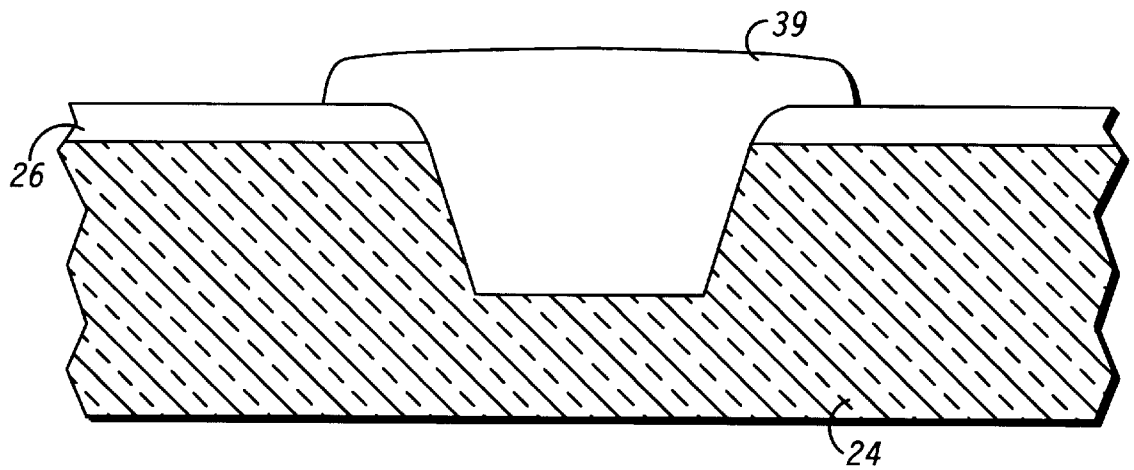

A sacrificial layer is formed over the first isolation layer 26 so as to fill the trench 25. The sacrificial layer is then etched to remove the portions of the sacrificial layer on the first isolation layer 26 and so as to leave a portion 39 filling the trench 25. It is not however necessary to remove all the sacrificial layer from the first isolation layer 26. As shown in FIG. 12, the portion 39 of the sacrificial layer may also extend across the first isolation layer 26.

Figure 13:
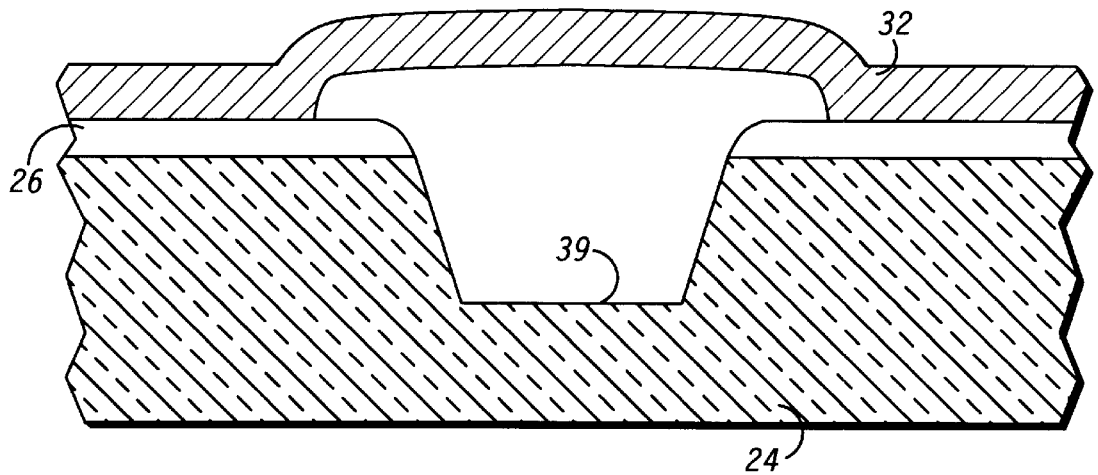

A conductive layer 32 is formed over the first isolation layer 26 and partly over the portion 39 of sacrificial layer so as to leave part of the portion 39 of the sacrificial layer exposed for subsequent etching (FIG. 13). The portion 39 of the sacrificial layer is then selectively etched using an isotropic etch (a vertical and lateral etch), preferably using a liquid etchant. The type of etchant used depends on the materials of the sacrificial layer, first isolation layer 26 and conductive layer 32. If, for example, the sacrificial layer comprises a polyimide layer, the first isolation layer comprises a silicon nitride layer and the conductive layer comprises a polysilicon layer, liquid hydrogen fluoride can be used as the etchant to selectively etch the portion of the polyimide sacrificial layer. Other materials such as SOG and silicon oxide may be used to form the sacrificial layer to fill the trench.

After selectively removing the portion 39 of the sacrificial layer, a cavity 30 is provided between the conductive layer 32 and the bottom of the trench 25 in the substrate 24: that is, the conductive layer 32 forms a bridge 28.

A second isolation layer 34, for example a silicon oxide layer, is formed over the conductive layer 32 and a sensitive layer 36 is formed over the second isolation layer 34 (FIG. 9).

Figure 14:
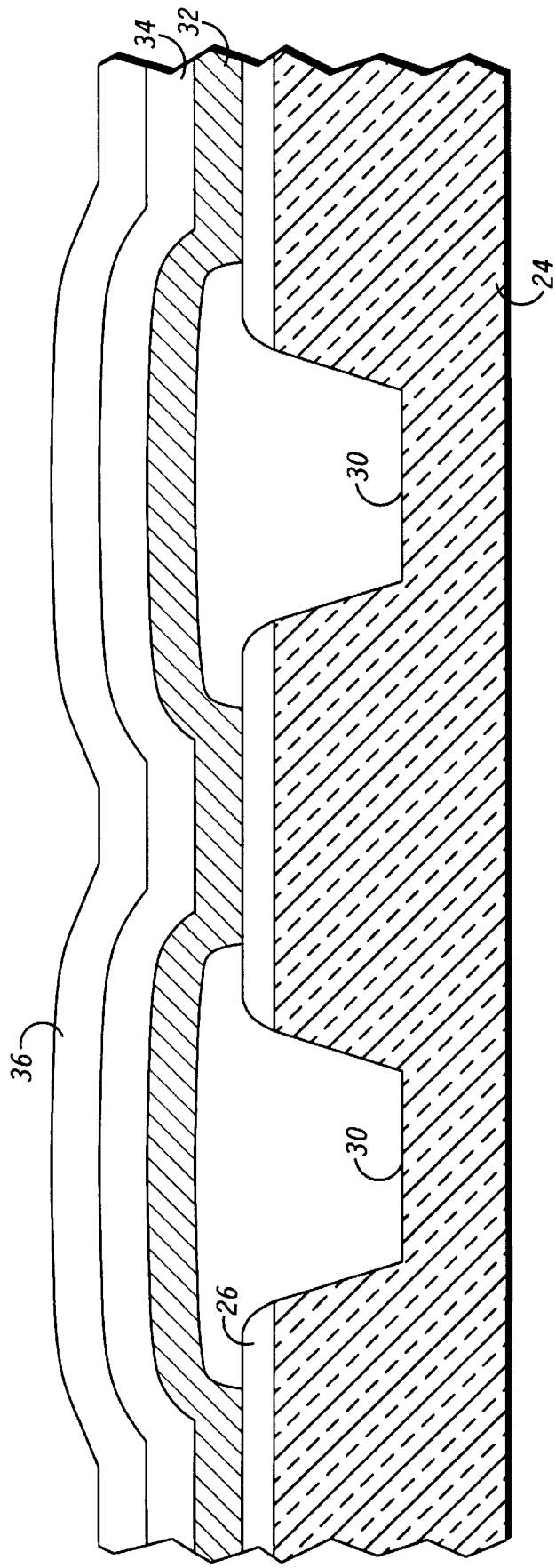
FIG. 14 shows a simplified schematic cross-sectional view of an alternative embodiment of the semiconductor sensor device shown in FIG. 9.

The semiconductor sensor device in accordance with the second embodiment of the invention has so far been described having one cavity 30. However, as with the first embodiment, the sensor device in accordance with the second embodiment may comprise two or more cavities, as shown for example in FIG. 14.

In order to form such a sensor device, the above method is modified such that two trenches are formed and filled with sacrificial material, which material is then selectively etched.

Figure 15:
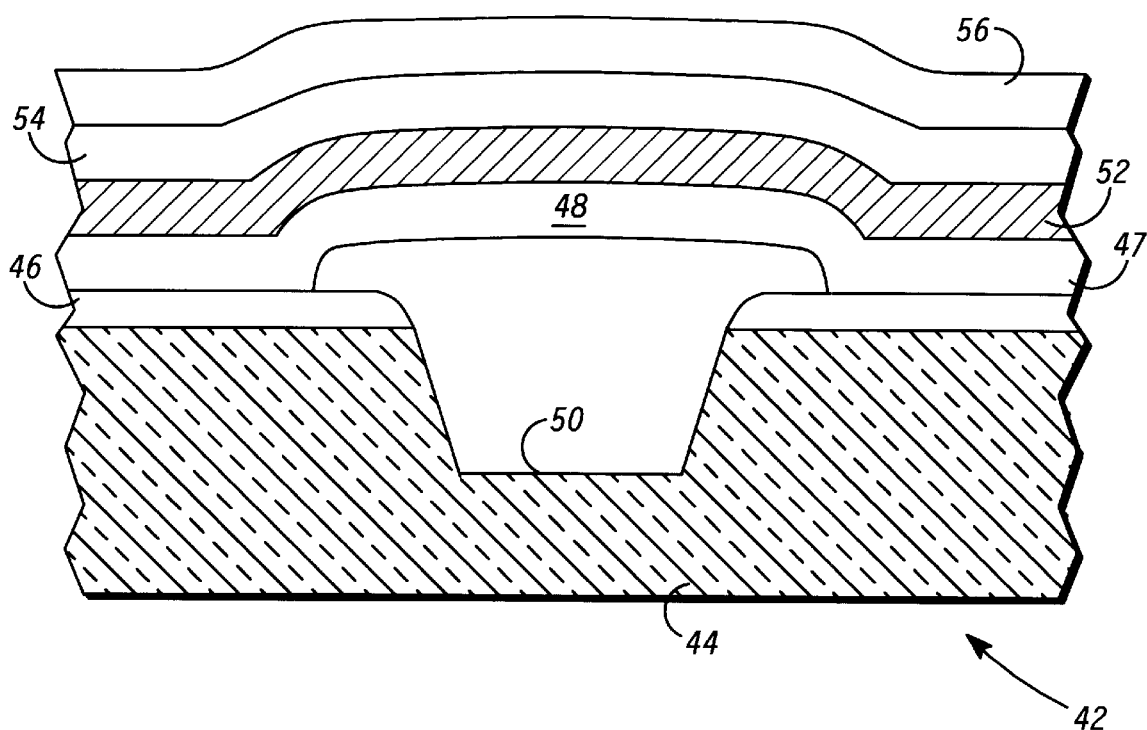
FIG. 15 shows a simplified schematic cross-sectional view of a semiconductor sensor device in accordance with a third embodiment of the present invention.

Referring now to FIG. 15, a semiconductor sensor device 42 in accordance with a third embodiment of the present invention is similar to the semiconductor sensor device 22 in accordance with the second embodiment except that a third isolation layer 47, for example a silicon nitride layer, is formed between the first isolation layer 46 and the conductive layer 52. In FIG. 15, like layers to those shown and described with reference to FIGS. 9–14 are referred to by the same reference numeral plus the number 20.

The method of forming the semiconductor sensor device 42 in accordance with the third embodiment is similar to the method of forming the semiconductor sensor device 22 in accordance with the second embodiment described above. Additional steps are required to form the third isolation layer 47 over the first isolation layer 46 and portion of sacrificial material filling the trench. The portion of sacrificial layer is selectively etched after forming the conductive layer 52 over the third isolation layer 47. This process may be modified to provide two or more cavities 50 as discussed above.

The second and third embodiments of the present invention are similar to the first embodiment in that an isolation layer or conductive layer, which forms the membrane of the sensor device, is formed on a sacrificial layer which is then selectively etched so as to provide at least one cavity. As mentioned above, this provides reduced heat loss and reduced power consumption without suffering from the problems of the prior art devices. The second and third embodiments, however, use an additional step of first etching the substrate to provide at least one trench before depositing the sacrificial layer and so these embodiments have deeper cavities compared to the first embodiment. Having a deeper cavity can improve the thermal isolation between the membrane and substrate.

In the above description, certain regions and layers are identified as being of particular material. However, this is merely for convenience of explanation and not intended to be limiting.

We claim:

1. A method for forming a semiconductor sensor device comprising the steps of:

providing a substrate;

forming a sacrificial layer over the substrate;

removing part of the sacrificial layer to leave a portion on the substrate;

forming a first isolation layer over the substrate and the portion of the sacrificial layer;

forming a conductive layer over the first isolation layer;

selectively etching the portion of the sacrificial layer to form a cavity between the first isolation layer and the substrate, the cavity providing thermal isolation therebetween;

forming a second isolation layer over the conductive layer; and forming a chemically sensitive layer over the second isolation layer.

2. A method for forming a semiconductor sensor device in accordance with claim 1 wherein the removing step comprises patterning and etching the sacrificial layer to leave first and second portions on the substrate, and wherein the selectively etching step comprises selectively etching the first and second portions of the sacrificial layer to provide first and second cavities between the first isolation layer and the substrate.

3. A method for forming a semiconductor sensor device in accordance with claim 1 wherein the selective etching step uses an isotropic selective etch of the portion of the sacrificial layer.

4. A method for forming a semiconductor sensor device in accordance with claim 1 wherein the selective etching step uses a liquid etchant.

5. A method for forming a semiconductor sensor device in accordance with claim 1 wherein the conductive layer comprises polysilicon material, the first isolation layer comprises silicon nitride and the selective etch step comprises etching the sacrificial layer with liquid hydrogen fluoride.

6. A method for forming a semiconductor sensor device in accordance with claim 1 wherein the material from which the sacrificial layer is formed is selected from the group of silicon dioxide, polyimide and SOG.

7. A method for forming a semiconductor sensor device comprising the steps of:

providing a substrate;

forming a first isolation layer over the substrate;

removing part of the first isolation layer and substrate to form a trench;

filling the trench with sacrificial material;

forming a conductive layer over the first isolation layer and sacrificial material in the trench;

selectively etching the sacrificial material in the trench to form a cavity between the conductive layer and the substrate to provide thermal isolation therebetween;

forming a second isolation layer over the conductive layer; and forming a chemically sensitive layer over the second isolation layer.

8. A method for forming a semiconductor sensor device in accordance with claim 7 wherein the removing part of the first isolation layer and substrate step comprises the step of etching the first isolation layer and substrate to form first and second trenches, and wherein the step of selectively etching comprises the step of selectively etching sacrificial material in the first and second trenches to form first and second cavities between the conductive layer and the substrate.

9. A method for forming a semiconductor sensor device in accordance with claim 7 wherein the method further comprises the step of forming a third isolation layer underneath the conductive layer.

10. A method for forming a semiconductor sensor device in accordance with claim 7 wherein the selective etching step uses an isotropic selective etch of the sacrificial material in the trench.

11. A method for forming a semiconductor sensor device in accordance with claim 7 wherein the selective etching step uses a liquid etchant.

12. A method for forming a semiconductor sensor device in accordance with claim 7 wherein the conductive layer comprises polysilicon material, the first isolation layer comprises silicon nitride and the selective etch step comprises etching the sacrificial material in the trench with liquid hydrogen fluoride.

13. A method for forming a semiconductor sensor device in accordance with claim 7 wherein the material from which the sacrificial layer is formed is selected from the group of silicon dioxide, polyimide and SOG.

* * * * *